United States Patent [19]

Genese

[11] 4,180,070
[45] Dec. 25, 1979

[54] DISPOSABLE DOUBLE VIAL SYRINGE

[75] Inventor: Joseph N. Genese, Waukegan, Ill.

[73] Assignee: Abbott Laboratories, North Chicago, Ill.

[21] Appl. No.: 828,686

[22] Filed: Aug. 29, 1977

[51] Int. Cl.² .............................................. A61M 5/00
[52] U.S. Cl. .............................. 128/218 M; 128/272.1
[58] Field of Search ............. 128/272.1, 272.3, 218 M, 128/220, 215, 216, 247; 141/311 R, 312, 2, 27, 388

[56] References Cited

U.S. PATENT DOCUMENTS

| | | | |
|---|---|---|---|
| 3,993,063 | 11/1976 | Larrabee | 128/272.3 |
| 3,995,630 | 12/1976 | Veerdonk | 128/272.1 X |
| 4,031,895 | 6/1977 | Porter | 128/272.1 |
| 4,060,082 | 11/1977 | Lindberg et al. | 128/272.1 X |

Primary Examiner—John D. Yasko
Attorney, Agent, or Firm—Neil E. Hamilton; Robert L. Niblack

[57] ABSTRACT

A preloaded, readily activated, disposable syringe wherein a first fluid diluent is sealed in a vial and is adapted to be received by a holding means in a syringe barrel. A second vial containing a fluid medicament is adapted to be engaged by a second holding means in the form of an adapter which is movable over the outside of the syringe barrel. A double-pointed cannula is positioned in the syringe barrel and has a hub with two frictional stop portions in conjunction with the syringe barrel. Upon movement of the adapter in the direction of the syringe barrel, one end of the cannula will pierce through the stopper secured to the adapter. Upon further movement of the adapter, it will contact the cannula hub and move it from a first retentive position to a second to thereby pierce the second stopper and provide fluid communication between the two vials. After mixing, the vial secured to the adapter will be emptied by moving it in a direction toward the syringe. This movement will then load the syringe vial with all of the medicament material. The adapter with its vial is then removed and the syringe is utilized in the usual manner.

17 Claims, 8 Drawing Figures

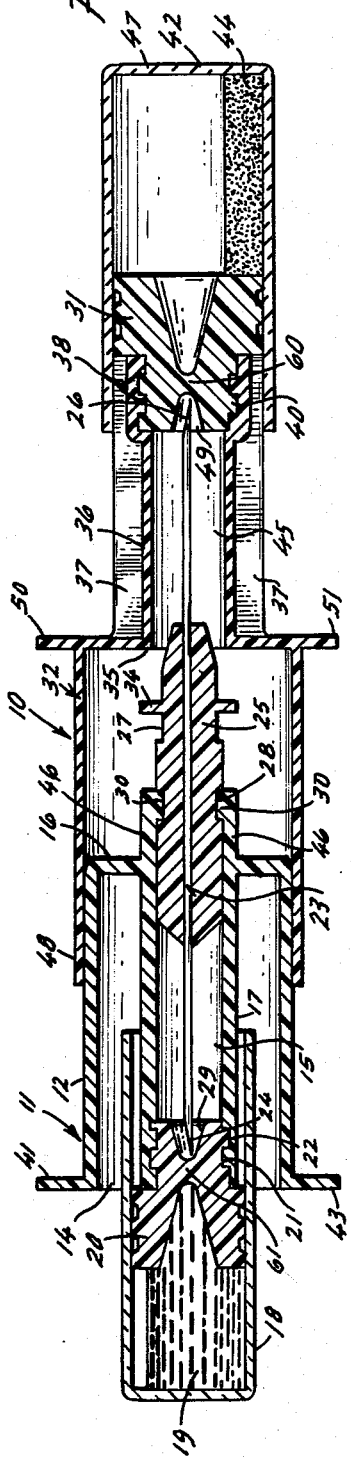
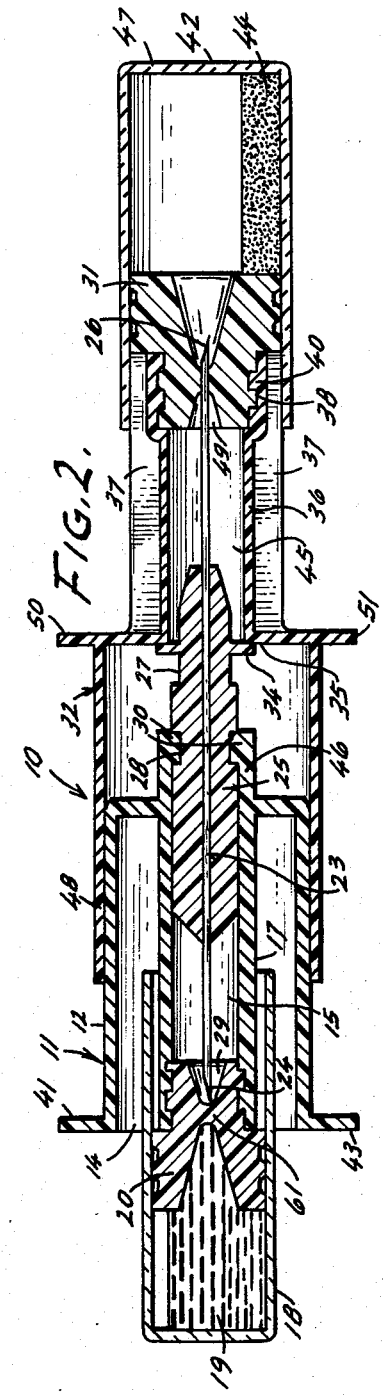
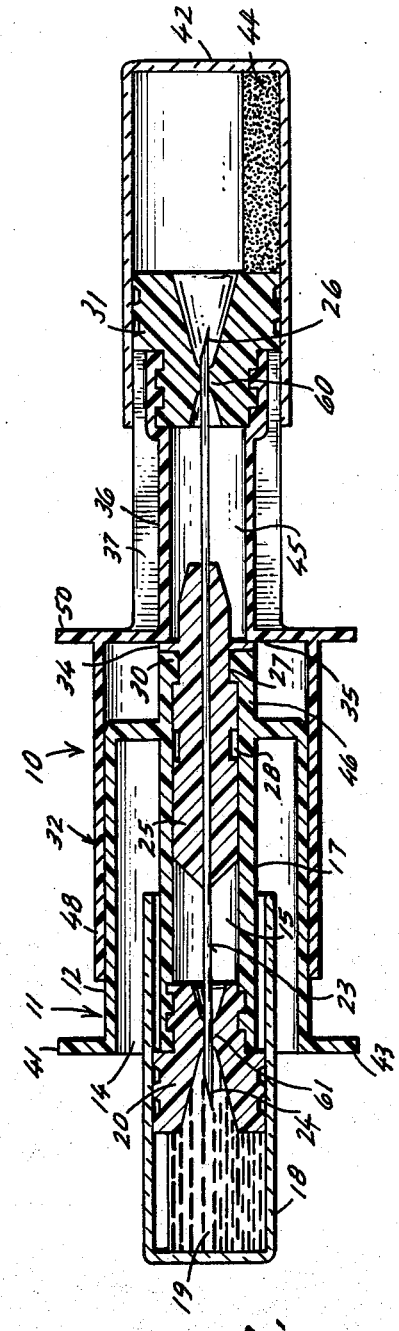

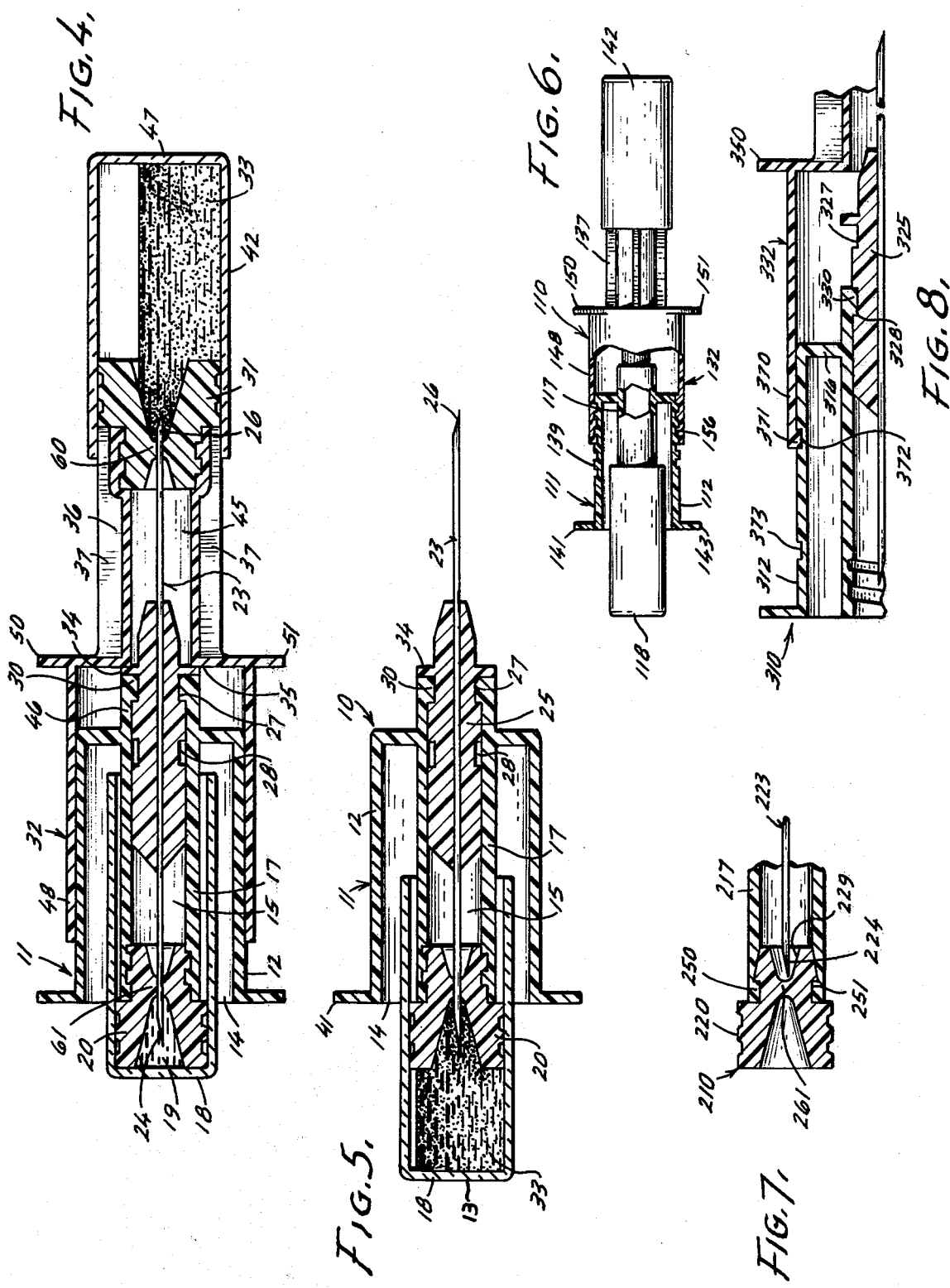

DISPOSABLE DOUBLE VIAL SYRINGE

BACKGROUND OF THE INVENTION

This invention relates to a disposable syringe wherein two incompatible materials are contained in separate vials until prior to usage. More particularly, it relates to a disposable syringe wherein one vial is received in the syringe body which also accommodates a double-pointed cannula having a hub member and a second vial is retained by an adapter which fits over the outside of the syringe barrel to provide upon movement of the adapter over the syringe barrel fluid communication between the two vials and intermixing of the two components.

Many types of disposable mixing syringes containing a dry medicament and a solvent for it are currently available. However, many such units are expensive to manufacture in that they require a multiplicity of parts and/or require several manipulations of the components in order to afford thorough mixing of the medicament with the solvent. In U.S. Pat. Nos. 3,327,710; 3,336,924; 3,397,694; 3,542,023; 3,636,950 and 3,659,602 syringes of the type concerned with in this invention are disclosed in that they utilize a separately attached vial for intermixing through a cannula which is to be later utilized as the means for hypodermic injection or a two-vial system wherein the contents of both vials are consolidated into one and then the one vial utilized as a hypodermic syringe. U.S. Pat. Nos. 3,327,710; 3,336,924 and 3,397,694 indicate syringe systems wherein the contents of an externally disposed vial are emptied into and mixed with the contents of a syringe. These systems are costly to manufacture and do not always provide proper sealing and subsequent communication with the vials because of the types of piercing of a stopper or the removal of a plug member to provide the necessary communication. The same problems with multi-component parts and positive piercing can be seen in the disposable cartridge for admixing with two components in U.S. Pat. No. 3,636,950. In U.S. Pat. Nos. 3,542,023 and 3,659,602 double vial systems are indicated for usage in a two-component syringe. However, these units do not lend themselves to a prepackaged and preloaded syringe system in that the adapter for the second vial extends outwardly a substantial distance from the syringe and subsequently when the second vial is attached, the system is awkward to handle and requires the manipulation of several components. Further, cost considerations are involved in special molding techniques for the specially designed post as in the 3,659,602 patent or the manipulation of several components to afford positive puncture of the two vials as in the 3,542,023 unit.

It is an advantage of the present invention to afford a novel syringe for mixing of a dry and a fluid component prior to usage with a minimum manipulation of steps and components. Other advantages are a double vial syringe unit which will afford maximum sealing of the two component materials from each other, positive puncture of the two vial stoppers with movement of one vial toward the other, preassembly of the two vials prior to usage and in a compact manner which will permit ease in packaging and a syringe unit which is easy to fabricate from a molding standpoint and thus less costly to manufacture which therefore lends itself to being disposable.

SUMMARY OF THE INVENTION

The foregoing advantages are accomplished and the shortcomings of the prior art are overcome by the present readily activated and disposable syringe which utilizes two separate vials and a double-pointed piercing cannula for piercing through the stoppers of each vial while providing fluid communication between them. The double-pointed cannula has a hub member with a two-frictional stop position for engagement by an annular flange in the syringe. An adapter housing fits over the outer wall of the syringe barrel for movement thereover. The syringe is packaged with one of the two vials secured to the syringe and the other to the adapter holder means in a first nonpiercing, yet second slidable relationship with the double-pointed piercing cannula. When it is desired to activate the system, all that is required is movement of the vial adapter toward the syringe which will effect a piercing of that stopper's vial. Continued movement of the adapter will cause the adapter housing to contact the hub portion of the cannula to effect piercing of the vial held in the syringe barrel. Fluid communication and mixing is then effected between the two vials. Upon movement of the vial held by the adapter toward the syringe barrel, its contents will be expelled into the vial on the syringe whereupon the vial connected to the adapter and the adapter are removed from the syringe barrel and the syringe is utilized in the usual manner.

BRIEF DESCRIPTION OF DRAWING

A better understanding of the present readily activated syringe will be afforded by reference to the drawing wherein:

FIG. 1 is a view in vertical section showing the hypodermic syringe of this invention in a prepackaged condition.

FIGS. 2, 3 and 4 are similar to FIG. 1 except showing the various stages of activating the syringe.

FIG. 5 is a view in vertical section showing the syringe of this invention with one of the vials and the adapter removed and ready for injection.

FIG. 6 is a view in side elevation with parts broken away illustrating an alternative embodiment.

FIG. 7 is a partial view in vertical section showing still another alternative embodiment.

FIG. 8 is a partial view in vertical section showing a further alternative embodiment.

DESCRIPTION OF THE EMBODIMENTS

The prefilled readily activated syringe generally 10 is composed of a holder 11 having a barrel portion 12 and an open end 14. A central passageway 15 is provided by means of a tubular chamber 17 which interconnects with the barrel 12 by means of end wall portion 16. A small volume container 18 in the form of a vial contains a medicinal diluent 19 and is sealed by a container stopper 20 which is attached on tubular chamber 17 by means of chamber internal threads 21 and stopper external threads 22. A double-pointed piercing cannula member 23 with piercing points 24 and 26 is secured in a hub 25, a portion of which is disposed in central passageway 15. It will be seen that tubular chamber 17 defines a plurality of resilient finger members 46 with arcuate flanges 30 for engagement in annular groove 28 of hub 25. Also disposed in hub 25 is an annular groove 27 which is formed in part by a contact flange 34.

An adapter 32 having a cylindrical portion 48 is slidably positioned on barrel 12 and has an extension or holding means 36 with guide arm or rib portions 37 for slidable engagement with the inside of vial 42. It will be recognized that adapter 32 will be slightly secured to barrel 12 such as by a slight bonding or tack welding. A shoulder section 35 connects cylindrical portion 48 with extension arm portions 37. A passage 45 is provided centrally of the arm portions which terminate in internal threads 38 for attachment with external threads 40 of stopper 31. As best seen in FIG. 1, piercing point 26 is accommodated in conical passage 49 of stopper 31 whereas the opposing pointed end 24 is similarly accommodated in a conical passage 29 of stopper 20 when the syringe is in an inactivated position. Vial 42 will contain a flowable medicinal material 44 which in this instance is preferably a powdered flowable material such as a general anesthetic.

Referring to FIG. 6, all of the previous components would be utilized in this alternative embodiment as indicated for syringe unit 10. Similar parts are indicated by similar numbers except that they are in the "100" series. The only difference between this unit 100 and the previously described syringe unit 10 is the provision of external threads 139 on holder 111 or syringe barrel 112 and complementary internal threads 156 disposed in cylindrical portion 148 of adapter 132. The purpose of the threaded engagement will be explained during the Operation of this particular unit.

In FIG. 7, another alternative embodiment is described and similar numbers are used for similar parts except that they are in the "200" series. This particular embodiment 210 illustrates an alternative method of securing stopper 220 to tubular chamber 217. Instead of the threaded engagement which would be utilized in unit 10, an annular flange 250 is provided for engaging an annular groove 251 in stopper 220. This type of frictional fitment could be employed also for the engagement of adapter 32 with stopper 31.

FIG. 8 illustrates another means for retentive movement of an adapter 332 over barrel 312 with corresponding parts referred to by similar numbers except in the "300" series. In this syringe unit 310, expanding finger members such as 370 having flanges 371 will frictionally engage groove 372 in barrel 312 when in a forward position and groove 373 when in an activated one.

Operation

A better understanding of the advantages of the readily activated syringes 10, 110, 210 and 310 will be had by a description of their operation. Referring first to unit 10, it will be packaged as indicated in FIG. 1 with the container vial 18 sealingly holding a diluent for the powdered medicament 44 sealed in container 42. It will be noted that the medicinal material 44 will be held in a sterile condition by means of puncturable stopper 31 and similarly diluent 19 is held in a similar condition in vial 18. The stoppers 20 and 31 will be positioned such that the points 24 and 26 of double-pointed piercing cannula 23 will be disposed in conical passages 29 and 49, respectively, and out of piercing contact with the stoppers. In this manner, the diluent 19 and the medicament 44 are out of contact with each other.

When it is desired to utilize unit 10, all that is required is a movement of small volume container 42 in the direction of adapter 32. This can be effected by placement of one's thumb on the end 47 of vial 42 and the fingers over grips 50 and 51 which will cause the cylindrical portion 48 of adapter 32 to break away from and slide over syringe barrel 12 until shoulder 35 contacts flange 34. When this contact between shoulder 35 and flange 34 occurs, point 26 of cannula 23 will have pierced through diaphragm section 60 of stopper 31 to position point 26 in contact with medicinal powder 44 as best seen in FIG. 2.

The next sequence of operation is in further movement of vial 42 toward adapter 32 which by means of contact between shoulder 35 and flange 34 will cause arcuate flanges 30 to ride up and out of annular groove 28 and into annular groove 27 adjacent contact flange 34 as hub 25 slides in passageway 15. When the previously described movement of flanges 30 occurred, the cylindrical portion 48 of adapter 32 will have moved further over the outside of syringe barrel 12 until it assumes a position as shown in FIG. 3. During movement of the previously described components, point 24 of cannula 23 will have pierced through diaphragm section 61 of stopper 20 to assume a position shown in FIG. 3 and in contact with diluent 19. In the position shown in FIG. 3, it will be noted that fluid communication is made between medicament 44 and diluent 19 by means of the hollow, tubular double-pointed piercing cannula 23.

In the next sequence, container 18 will be moved in a sliding manner inwardly into holder 11 and over tubular chamber 17. This is facilitated by placement of one's thumb on the end 13 of vial 18 and the fingers over grips 41 and 43. As stopper 20 slides inside vial 18 this causes most of the medicament to flow from container 18 into container 42 where the combined diluent and powder will be mixed and is indicated by the numeral 33. After thorough mixing such as by shaking the syringe, container 42 will be moved in a sliding manner over holding arms 37 in the direction of syringe barrel 12 so that upon movement of stopper 31 inside container 42 and toward end 47 the combined diluent diluent and medicament 33 will be returned to container 18. This will cause container 18 to move outwardly from the syringe barrel 12 and over tubular chamber 17 until it assumes a position as shown in FIG. 5. At this point, adapter 32 and vial container 42 will be removed from the syringe barrel 12. The syringe unit 10 will be ready for injection in the usual manner by placing the fingers on finger grips 41 and 43 with the thumb on the end portion 13 of container 18. Double-pointed cannula with point 26 now functions as a hypodermic needle.

Syringe units 110 and 310 are operable in a manner similarly described for unit 10 except that in place of the sliding action of adapter 32 over syringe barrel 12, a threaded action is accomplished for movement of adapter 132 over syringe barrel 112 in the 110 unit by means of internal threads 156 and external threads 139. This threaded action will take place throughout the piercing of both stoppers such as 20 and 31 during movement of corresponding shoulder 35 toward corresponding flange 34 as well as the movement of flanges such as 30 out of annular groove such as 28 and into corresponding groove 27, as previously described for unit 10. In the syringe unit 310, movement of adapter 332 over syringe 312 will be effected as flanges 371 moves from groove 372 to groove 373 to effect the previously described contact between adapter 332 and hub 325 and piercing of stoppers corresponding to 20 and 31.

The FIG. 7 embodiment, 210 does not require a full explanation of its operation as it merely shows an alternative means of securing a stopper 220 to tubular chamber 217 which could be utilized in the previous embodiments for the threaded engagement such as between the tubular chamber 17 and stopper 20 or stopper 31 and arm portions 37 of extension 36.

In the foregoing description, it will be recognized that in order to facilitate the movement of annular flanges 30 out of annular groove 28, a chamfered surface could be utilized between the forward ends of flanges 30 and groove 28. It will be further recognized that a dual function is served in the utilization of contact flange 34 in that it serves as a stop member for adapter 32 by contact with shoulder 35 as well as contact with the end of tubular chamber 17 when flanges 30 seat in groove 27.

The preferred materials for composing holder 11 and adapter 32 is polypropylene. However, acrylonitrile-butadiene-styrene could be used alternatively. The preferred materials for fabricating hub 25 as well as the double-pointed piercing cannula 23 are polyvinyl chloride and stainless steel respectively. However, other hub materials such as acrylonitrile-butadiene-styrene and acetal could be utilized. For stability purposes, container vials 18 and 42 are formed from glass. If desired, translucent or clear plastic could be used. The associated stoppers 20 and 31 are formed from a resilient, pierceable rubber or plastic material.

It will thus be seen that through the present invention there is now provided a prefilled, readily activated syringe system which can be packaged in an assembled condition and readily activated with a minimum number of steps. Complete mixing can be afforded through effective sequencing of the syringe unit. At the same time, a minimum number of parts are required to fabricate the syringe, which parts can be molded without expensive molding techniques or materials. As all of the components can be fabricated from relatively inexpensive materials, the syringe system is disposable.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

I claim:

1. A prefilled, readily activated syringe comprising:
   a first holding means defining a syringe barrel with an open end and a central passageway;
   a first small volume container having a medicament or diluent therefor constructed and arranged to be engaged by said holding means in a sliding relationship;
   a pierceable stopper in sealing and slidable engagement with said first container;
   a double-pointed piercing cannula member having a hub portion disposed in said central passageway;
   means operatively associated with said hub and said central passageway defining at least two frictional stop positions for said cannula hub;
   an adapter housing constructed and arranged for movable engagement over said syringe barrel;
   a first contact surface operatively associated with said cannula hub;
   a second surface operatively associated with said adapter housing for engagement with said first contact surface;
   a second holding means for a second small volume container extending from said adapter housing and having a passage therethrough for said cannula;
   a second small volume container having a differing medicament or diluent from that in said first container, said container constructed and arranged to be engaged by said second holding means in a sliding relationship; and
   a pierceable stopper in sealing and sliding engagement with said second container;
   said first and second holding means constructed and arranged with respect to said containers to position said container stoppers out of contact with the piercing points of said cannula in one position and to afford piercing of both stoppers when said adapter housing is moved in a direction toward said first container so that said second container vial is pierced first and upon further movement of said adapter housing said first and second contact surfaces will engage to effect movement of said cannula hub with respect to said central passageway of said syringe barrel by means of said frictional stop positions to effect a piercing of said stopper in said first container whereby fluid communication is established between said containers to effect mixing of said medicament and said diluent with expulsion of said mixture from said syringe after removal of said adapter and said second container.

2. The prefilled readily activated syringe as defined in claim 1 wherein said means operatively associated with said hub and said central passageway defining two frictional stop positions for said cannula hub is defined by arcuate flanges extending from said syringe barrel and by stop surfaces carried by the hub.

3. The prefilled readily activated syringe as defined in claim 2 wherein said stop surfaces carried by said hub are defined by groove portions.

4. The prefilled readily activated syringe as defined in claim 1 wherein said first holding means for said first container is defined by an inner chamber with a portion of said hub portion disposed therein and having attachment means for maintaining said stopper of said first container in a stationary manner and additional attachment means carried by said second holding means adjacent the end of said passage for maintaining said stopper of said second container in a stationary manner.

5. The prefilled readily activated syringe as defined in claim 4 wherein said stoppers of said first and second container vials are threaded and said attachment means of said first and second holding means are also threaded for complementary interengagement.

6. The prefilled readily activated syringe as defined in claim 4 wherein said stoppers of said first and second container vials and said attachment means of said first and second holding means are defined by a complementary frictional fitment.

7. The prefilled readily activated syringe as defined in claim 2 wherein said movable engagement of said adapter housing over said syringe barrel is defined by a slide fitment.

8. The prefilled readily activated syringe as defined in claim 2 wherein said movable engagement of said adapter housing over said syringe barrel is defined by external threads carried by said syringe barrel and complementary internal threads carried by said adapter.

9. The prefilled readily activated syringe as defined in claim 2 wherein said central passageway is defined by a tubular chamber.

10. The prefilled readily activated syringe as defined in claim 2 wherein said second holding means extending from said adapter housing includes arm portions for guiding engagement with the inside of said second container.

11. The prefilled readily activated syringe as defined in claim 2 wherein said adapter housing and said second holding means are joined by a shoulder portion to provide said second engagement surface.

12. The prefilled readily activated syringe as defined in claim 1 wherein said syringe is packaged with said containers engaged by said holding means.

13. The prefilled readily activated syringe as defined in claim 1 wherein all of said components except said piercing cannula, said stoppers and said containers are composed of a plastic material and is disposable.

14. An adapter to provide communication between a small volume container and a syringe barrel member having an external wall with external thread means comprising:

- an adapter housing constructed and arranged for movable engagement over an external wall of the syringe barrel;
- a holding means for said small volume container extending from said adapter housing and having a passage therethrough for a hypodermic needle, said small volume container having a medicament or diluent therefor and constructed and arranged to be engaged by said holding means in a sliding relationship;
- internal thread means defined by said adapter for engagement with said syringe barrel thread means; and
- a pierceable stopper in sealing and slidable engagement with said container and adapted to be pierced by said hypodermic needle.

15. The adapter as defined in claim 14 wherein said holding means extending from said adapter housing includes guide ribs for guiding engagement with the inside of said container.

16. The adapter as defined in claim 14 wherein said adapter housing and said holding means are joined by a shoulder portion.

17. The adapter as defined in claim 14 wherein said holding means includes an attachment means in the form of a frictional fitment for engagement with said container.

* * * * *